(12) United States Patent
Azria et al.

(10) Patent No.: US 7,749,954 B2
(45) Date of Patent: Jul. 6, 2010

(54) USE OF CALCITONIN IN OSTEOARTHRITIS

(75) Inventors: Moise Azria, Basel (CH); Claus Christiansen, Ballerup (DK); Simon David Bateman, Randolph, NJ (US); Shoufeng Li, Basking Ridge, NJ (US)

(73) Assignee: Novartis AG, Basel (CH)

( * ) Notice: Subject to any disclaimer, the term of this patent is extended or adjusted under 35 U.S.C. 154(b) by 447 days.

(21) Appl. No.: 10/565,455

(22) PCT Filed: Jul. 22, 2004

(86) PCT No.: PCT/EP2004/008210

§ 371 (c)(1),
(2), (4) Date: Apr. 5, 2006

(87) PCT Pub. No.: WO2005/014031

PCT Pub. Date: Feb. 17, 2005

(65) Prior Publication Data

US 2006/0194722 A1    Aug. 31, 2006

Related U.S. Application Data

(60) Provisional application No. 60/489,400, filed on Jul. 23, 2003.

(51) Int. Cl.
*A61K 38/23* (2006.01)
*A61K 38/00* (2006.01)
*C07K 5/00* (2006.01)

(52) U.S. Cl. ............................. 514/2; 530/307; 530/300

(58) Field of Classification Search ........................ None
See application file for complete search history.

(56) References Cited

U.S. PATENT DOCUMENTS 5,912,014 A * 6/1999 Stern et al. .................. 424/474
6,352,974 B1 * 3/2002 Ghirri et al. .................. 514/12
2002/0065255 A1 * 5/2002 Bay et al. .................... 514/166

FOREIGN PATENT DOCUMENTS

JP    05 345729    12/1993
WO    00/59863    10/2000

OTHER PUBLICATIONS

Mongiorgi et al., Boll. Soc. Ital. Biol. Sper., 1992, 68(2):85-9.*
Shah et al., Endocrinology, 1994, vol. 134(2): 596-602.*
Chigurupati et al., Cancer Res., 2005, 65(18):8519-8529.*
Epand et al., Eur. J. Biochem., 1990, vol. 188:633-635.*
Kaplan et al., J. Am. Acad. Orthop. Surg., 1995, vol. 3(6):336-344.*
Mongiorgi et al., "Influence of Calcitonin Treatment on the Bone Structure and Mineral Content in Osteoarthritis", Bollettino Societa Italiana Biologia Sperimentale, vol. 68, No. 2, pp. 85-89 (1992).
Gospodinoff et al., "Calcitonin in Treatment of Coxarthrosis", Clinica Terapeutica, vol. 110, No. 2, pp. 129-133 (1984).
Consoli et al., "Calcitonin in Rheumatologie Osteoporosis Aspects and Prelimin Evaluation of Pathophysiology and Clinical Features", Clinica Terapeutica, vol. 118, No. 1, pp. 37-47 (1986).
Guggi et al., "In Vitro Evaluation of Polymeric Excipients Protecting Calcitonin Against Degradation by Intestinal Serine Proteases", International Journal of Pharmaceutics, vol. 252, No. 1-2, pp. 187-196 (2003); Database Medline 'Online', Abstract Database Accession No. NLM12550794.
Smethurst et al., "Combined Therapy with Ascorbic Acid and Calcitonin for the Relief of Bone Pain in Paget's Disease", ACTA Vitaminologica et Enzymologica, vol. 3, No. 1, pp. 8-11 (1981).
Lee et al., "Oral Delivery of Salmon Calcitonin", Advanced Drug Delivery Reviews, vol. 42, No. 3, pp. 225-238 (2000).
Hayami et al., "The Role of Subchondral Bone Remodeling in Osteoarthritis", Arthritis & Rheumatism, vol. 50, No. 4, pp. 1193-1206, (2004).
Tanko et al., "Safety and Efficacy of a Novel Salmon Calcitonin (sCT) Technology-Based Oral Formulation in Healthy Postmenopausal Women: Acute and 3-month Effects on Biomarkers of Bone Trunover", Journal of Bone and Mineral Research, vol. 19, No. 9, pp. 1531-1538, (2004).
Bingham et al., "Risedronate Decreases Biochemical Markers of Cartilage Degradation but Does Not Decrease Symptoms or Slow Radiographic Progression in Patients With Medial Compartment Osteoarthritis of the Knee", Arthritis & Rheumatism, vol. 54, No. 11, pp. 3494-3507, (2006).
Buclin et al., "Bioavailability and Biological Efficacy of a New Oral Formulation of Salmon Calcitonin in Healthy Volunteers", Journal of Bone and Mineral Research, vol. 17, No. 8, pp. 1478-1485, (2002).
Manicourt et al., "Treatment with Calcitonin Suppresses the Responses of Bone, Cartilage, and Synovium in the Early Stages of Canine Experimental Osteoarthritis and Significantly Reduces the Severity of the Cartilage Lesions", Arthritis & Rheumatism, vol. 42, No. 6, pp. 1159-1167, (1999).
Reagan-Shaw et al., "Dose translation from animal to human studies revisited", The FASEB Journal Life Sciences Forum, vol. 22, pp. 659-661, (2007).
Paget's Disease of Bone and Osteoarthritis: Different Yet Related, National Institutes of Health Osteoporosis and Related Bone Diseases, pp. 1-4, Revised Oct. 2005.
Kleinman, Denise Mann, "Oral Calcitonin May Delay Onset of Joint Disease and Relieve Pain of OA", Musculoskeletal Report, Jan. 4, 2006.

* cited by examiner

*Primary Examiner*—Elizabeth C. Kemmerer
*Assistant Examiner*—Xiaozhen Xie
(74) *Attorney, Agent, or Firm*—David R. Kurlandsky; Leslie Fischer

(57) ABSTRACT

The present invention relates to a novel use of calcitonin in osteoarthritis, and to methods of treating and/or preventing osteoarthritis in mammals, particularly humans.

11 Claims, No Drawings

000
USE OF CALCITONIN IN OSTEOARTHRITIS

This application claims benefit of U.S. Provisional Application No. 60/489,400, filed Jul. 23, 2003, which in its entirety is herein incorporated by reference.

BACKGROUND OF THE INVENTION

The present invention relates to a novel use of calcitonin in osteoarthritis, and to methods of treating and/or preventing osteoarthritis in mammals, particularly humans.

Calcitonins, e.g. salmon, (Asu 1-7)-eel or human calcitonin, of the invention are compounds which are long-chain polypeptide hormones secreted by the parafollicular cells of the thyroid gland in mammals and by the ultimobranchial gland of birds and fish. Calcitonin is mainly known as a potent inhibitor of osteoclastic bone resorption, which implicates bone attachment of osteoclasts and enzymatic degradation. Furthermore, it was found that there are effects of Intranasal Salmon Calcitonin in Juvenile Idiopathic Arthritis in humans (Siamopoulou A. et al, 2001, Calcif Tissue Int 69: 25-30) and in the prevention of bone erosion and bone loss in rheumatoid arthritis in humans (Sileghem A., 1992, Annals of Rheumatic Diseases 51: 761-764). The degradative process associates synthesis of various proteases and metalloproteinases, activation of inactive proenymes and inhibition of active enzymes (Leloup G, 1994, J Bone Miner Res, 9, 891-902). Calcitonin is known to induce osteoclast retraction (Zheng M H, et al., 1992, Exper Mole Pathol, 57: 105-115) and to interfere at least with some steps of the enzymatic process of bone resorption (Einhorn T A et al., 1991, Clin Orthop 262: 286-297). There are some reported studies on the effects of calcitonin on articular cartilage. In vitro, calcitonin was found to stimulate proteoglycan and collagen synthesis in animal epiphyseal cartilage (Baxter et al., 1984, Endocrinology 114: 1196-1202) as well as in rabbit and human cartilage (Franchimont P, 1989, J Clin End Metab 69: 259-266). The study of calcitonin in the treatment of experimental osteoarthritis gave conflicting results. E.g. calcitonin was found to prevent cartilage destruction in rabbits treated with steroids, partial menisectomy or joint immobilization (Badurski J E et al., 1991, Lab Invest 49: 27-34), but no effect on cartilage was observed in another menisectomy model (Colombo et al., 1983, Arthritis Rheum 26: 1132-1139). Moreover, the relative importance of cartilage and bone changes in the Initiation and progression of osteoarthritis is still being debated. No study in humans has yet shown to our knowledge the efficacy of calcitonin in osteoarthritis.

BRIEF SUMMARY OF THE INVENTION

In accordance with the present invention, it has now surprisingly been found that calcitonin, e.g. salmon, (Asu 1-7)-eel or human calcitonin are useful in the prevention and treatment of osteoarthritis in mammals, particularly humans. In particular, the oral delivery of calcitonin, e.g. salmon calcitonin or (Asu 1-7)-eel calcitonin, as described in the present invention shows such an effect. Said oral delivery of calcitonin is generally the delivery route of choice since it is convenient, relatively easy and generally painless, resulting in greater patient compliance relative to other modes of delivery.

In accordance with the particular findings of the present invention, there is provided:

1.1. A method of preventing or/and treating osteoarthritis in a patient in need thereof comprising administering to said patient a therapeutically effective amount of calcitonin, e.g. salmon calcitonin in free form or salt form, preferably in a pharmaceutically acceptable oral delivery form;

1.2 A method of preventing or/and treating osteoarthritis in a patient in need thereof comprising administering to said patient a therapeutically effective amount of calcitonin, e.g. salmon calcitonin in free form or salt form, preferably in a pharmaceutically acceptable oral delivery form, wherein the therapeutically effective amount of a calcitonin is delivered orally in a composition comprising the calcitonin and a delivery agent for calcitonin.

1.3 A method of preventing or/and treating osteoarthritis in a patient in need thereof comprising administering to said patient a therapeutically effective amount of calcitonin, e.g. salmon calcitonin in free form or salt form, preferably in a pharmaceutically acceptable oral delivery form, wherein the therapeutically effective amount of a calcitonin is delivered orally in a composition comprising the calcitonin which is conjugated to a polymer molecule.

1.4 A method of inhibiting resorption and normalizing turnover of sub-chondral bone in a patient in need thereof comprising administering to said patient a therapeutically effective amount of calcitonin; e.g. salmon calcitonin in free form or salt form, preferably in a pharmaceutically acceptable oral delivery form;

1.5 A method of preserving and stimulating cartilage via a direct or indirect effect on chondrocytes in a patent in need thereof comprising administering to said patient a therapeutically effective amount of calcitonin, e.g. salmon calcitonin in free form or salt form, preferably in a pharmaceutically acceptable oral delivery form;

1.6 A method of inhibiting phosphollpase A2 and/or collagenase activity in a patient in need thereof comprising administering to said patient a therapeutically effective amount of calcitonin, e.g. salmon calcitonin in free form or salt form, preferably in a pharmaceutically acceptable oral delivery form;

1.7 A method of stimulatory effect on glycosaminoglycan and/or proteoglycan synthesis in a patient in need thereof comprising administering to said patient a therapeutically effective amount of calcitonin, e.g. salmon calcitonin in free form or salt form, preferably in a pharmaceutically acceptable oral delivery form;

1.8 A method of acting on the inhomogeneity in density or stiffness of the subchondral bone in a patient in need thereof comprising administering to said patient a therapeutically effective amount of calcitonin, e.g. salmon calcitonin in free form or salt form, preferably in a pharmaceutically acceptable oral delivery form;

1.9 A method of acting on the inflammatory process, leading to attenuations on pain in motion and related symptoms (e.g. circumference of knee, flexion angle of the knee, swelling stiffness) in a patient in need thereof comprising administering to said patient a therapeutically effective amount of calcitonin, e.g. salmon calcitonin in free form or salt form, preferably in a pharmaceutically acceptable oral delivery form;

2.0 A method to reduce the degenerative change in the joint in a patient in need thereof comprising administering to said patient a therapeutically effective amount of calcitonin, e.g. salmon calcitonin in free form or salt form, preferably in a pharmaceutically acceptable oral delivery form;

2.1 A method as defined above, comprising co-administration of a therapeutically effective amount of calcitonin, e.g. salmon calcitonin in free form or salt form, preferably in a pharmaceutically acceptable oral delivery form, and a second drug substance, said second drug substance being a bone resorption inhibitor, bone forming drug or pain reducing drug in free form or salt form.

In another aspect, the invention provides a particular dosage range for a calcitonin, e.g. salmon calcitonin, which is efficacious and well tolerated, i.e. safe for a patient to take. Preferred is a range between 0.4 and 2.5 mg of salmon calcitonin for a patient, e.g. human, e.g. an average human of about 70 kg. More preferred are doses around 1 mg, e.g. between 0.8 and 1.2 mg. Also preferred are doses less than 1 mg but higher than 0.4 mg. Even more preferred is a dose of about 1 mg, e.g. 1 mg. Most preferred is a dose of about 1 mg, e.g. between 0.8 and 1.2 mg, administered once per day to a patient in need thereof. Pharmaceutical compositions comprising said doses according to the invention may be the compositions as provided in the Examples but may be preferably oral compositions, e.g. compositions as defined in Example 8. The dosage regimen may be once a day or twice a day, preferably one in the morning and one in the evening.

2.2 A method of preventing or/and treating osteoarthritis in a patient in need thereof comprising administering to said patient a pharmaceutical composition comprising between 0.4 and 2.5 mg, preferably between 0.8 and 1.2 mg, most preferred about 1 mg, of a calcitonin, e.g. salmon calcitonin.

2.3 A pharmaceutical composition comprising between 0.4 and 2.5 mg, preferably between 0.8 and 1.2 mg, most preferred about 1 mg of a calcitonin, e.g. salmon calcitonin.

2.4 The use of a calcitonin, e.g. salmon calcitonin, in the manufacture of a medicament for the treatment and/or prevention of osteoarthritis, wherein said calcitonin is provided in a pharmaceutical composition comprising between 0.4 and 2.5 mg, preferably between 0.8 and 1.2 mg, most preferred about 1 mg, of a calcitonin, e.g. salmon calcitonin.

2.5 A pharmaceutical composition for use in treating or/and preventing osteoarthritis comprising between 0.4 and 2.5 mg, preferably between 0.8 and 1.2 mg, most preferred about 1 mg, of a calcitonin, e.g. salmon calcitonin.

Suitable second drug substances may include a calcitonin of different origin, e.g. salmon, (Asu 1-7)-eel or human calcitonin, a calcitonin analogue or derivative thereof, a steroid hormone, e.g. an estrogen, a partial estrogen agonist or estrogen-gestagen combination, a SERM (Selective Estrogen Receptor Modulator) e.g. raloxifene, lasofoxifene, TSE424, FC1271, Tibolone (Livial®), vitamin D or an analogue thereof or PTH, a PTH fragment or a PTH derivative e.g. PTH (1-84), PTH (1-34), PTH (1-36), PTH (1-38), PTH (1-31) NH2 or PTS 893, bisphosphonates (e.g. alendronate, risedronate, zoledronic acid, ibandronate); protease inhibitors, e.g. Cathepsin inhibitor, preferably a cathepsin K inhibitor; PTH releasers; SARMs (selective androgen receptor molecules); MMP inhibitors (metalloprotease inhibitors), strontium ranelate, COX-2 inhibitors, e.g. lumiracoxib (Prexige®), celecoxib (Celebrex®), rofecoxib (Vioxx®), valdecoxib (Bextra®), etoricoxib (Arcoxia®), or mixed COX-1 and COX-2 inhibitors, e.g. diclofenac.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

As alternative to the above the present invention also provides:

3. A calcitonin, e.g. salmon, (Asu 1-7)-eel or human calcitonin in free form or salt form, preferably in a pharmaceutically acceptable oral delivery form, for use in any method as defined under 1.1 to 2.2 above; or 4. A calcitonin, e.g. salmon, (Asu 1-7)-eel or human calcitonin in free form or salt form, preferably in a pharmaceutically acceptable oral delivery form, for use in the manufacture of a medicament in any indications as defined under 1.1 to 2.2 above; or 5. A pharmaceutical composition for use in any indications as defined under 1.1 to 2.2 above comprising a calcitonin, e.g. salmon, (Asu 1-7)-eel or human calcitonin in free form or salt form, preferably in a pharmaceutically acceptable oral delivery form, together with one or more pharmaceutically acceptable diluents or carriers therefore.

6. A pharmaceutical combination comprising:

a) a first agent which is a calcitonin, e.g. salmon, (Asu 1-7)-eel or human calcitonin in free form or salt form, preferably in pharmaceutically acceptable oral delivery form, and b) a co-agent which is bone resorption inhibitor, bone forming drug or pain reducing agent, e.g. as disclosed above.

7. A kit of parts fur use in the prevention and/or treatment of osteoarthritis, said kit comprising:

a) a first agent which is a calcitonin, e.g. salmon, (Asu 1-7)-eel or human calcitonin in free form or salt form, preferably in pharmaceutically acceptable oral delivery form, and b) a co-agent which is bone resorption inhibitor, bone forming drug or pain reducing agent, e.g. as disclosed above.

DETAILED DESCRIPTION OF THE INVENTION

The term "patient" as used herein means a patient in need of being treated or prevented from osteoarthritis or any method as defined under 1.1 to 2.2 above, whereas patient means mammals, such as rodents, cows, pigs, dogs, cats, and primates, particularly humans.

The term "pharmaceutical combination" as used herein means a product that results from the mixing or combining of more than one active ingredient and includes both fixed and non-fixed combinations of the active ingredients. The term "fixed combination" means that the active ingredients, e.g. salmon calcitonin and a co-agent, are both administered to a patient simultaneously in the form of a single entity or dosage. The term "non-fixed combination" means that the active ingredients, e.g. salmon calcitonin and a co-agent, are both administered to a patient as separate entities either simultaneously, concurrently or sequentially with no specific time limits, wherein such administration provides therapeutically effective levels of the 2 compounds in the body of the patient.

Preferably the calcitonin, e.g. salmon calcitonin in free form or in pharmaceutically acceptable salt form, is co-administered with a protease inhibitor, e.g. cathepsin inhibitor, e.g. cathepsin K inhibitor.

Utility of calcitonin, e.g. salmon calcitonin in free form or salt form, preferably in pharmaceutically acceptable oral delivery form for use in any method as defined under 1.1 to 1.10, may be demonstrated in animal test methods as well as in clinic, for example in accordance with the method hereinafter described in Example B.

When the pharmacologically active agent is salmon calcitonin, the appropriate dosage will, of course, vary depending upon, for example, the host and the nature and severity of the condition being treated. However, in general, satisfactory results will be obtained systemically at daily dosages of from about 0.5 µg/kg to about 10 µg/kg animal body weight, preferably 1 µg/kg to about 6 µg/kg body weight. The pharmaceutically acceptable inactive excipients which are used in the formulation of calcitonin, e.g. in the oral formulation of calcitonin, may include polymers and inactive compounds which for example, aid the formulation or manufacturing of the solid oral dosage form contemplated by the present invention or which may aid the release of the solid oral composition in the gastro-intestinal environment. The pharmaceutically inactive ingredients, referred to above, for example optionally include crospovidones and povidones, which may be any crospovidone and povidone. Crospovidone is a synthetic crosslinked homopolymer of N-vinyl-2-pyrrolidone, also called 1-ethenyl-2-pyrrolidinone, having a molecular weight of 1,000,000 or more. Commercially available crospovidones include Polyplasdone XL, Polyplasdone XL-10, Polyplasdone INF-10 available from ISP, Kollidon CL, available from BASF Corporation. The preferred crospovidone is Polyplasdone XL. Povidone is a synthetic polymer consisting of linear 1-vinyl-2-pyrrolidinone groups having a molecular weight generally between 2,500 and 3,000,000. Commercially available povidones include Kollidon K-30, Kollidon K-90F available from BASF Corporation and Plasdone K-30 and Plasdone K-29/32, available from ISP. As mentioned above, the crospovidones and povidones are commercially available. Alternatively, they may be synthesized by known processes. The crospovidone, povidone or combination thereof is generally present in the compositions in an amount of from 0.5 to 50 percent by weight relative to the total weight of the overall pharmaceutical composition, preferably an amount of from 2 to 25 percent, more preferably 5 to 20 percent by weight relative to the total weight of the pharmaceutical composition.

The delivery agents useful in the formulation, e.g. the oral formulation, are any agents useful for delivering the particular pharmacologically active agent. Suitable delivery agents are any one of the modified amino acids disclosed in aforementioned U.S. Pat. No. 5,866,536 or any one of the modified amino acids described in the aforementioned U.S. Pat. No. 5,773,647 or any combination thereof. The contents of the aforementioned U.S. Pat. Nos. 5,773,647 and 5,866,536 are hereby incorporated by reference in their entirety. In addition, the delivery agent can be the disodium salt of any of the aforementioned modified amino acids as well as ethanol solvates and hydrates thereof. Suitable compounds include compounds of the following formula I

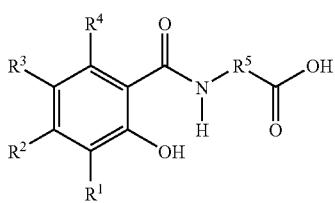

Formula 1 wherein
$R^1$, $R^2$, $R^3$, and $R^4$ are independently hydrogen, —OH, —$NR^6R^7$, halogen, $C_1$-$C_4$alkyl, or $C_1$-$C_4$alkoxy;
$R^5$ is a substituted or unsubstituted $C_2$-$C_{16}$alkylene, substituted or unsubstituted $C_2$-$C_{16}$alkenylene, substituted or unsubstituted $C_1$-$C_{12}$alkyl(arylene), or substituted or unsubstituted aryl($C_1$-$C_{12}$alkylene); and
$R^6$ and $R^7$ are independently hydrogen, oxygen, or $C_1$-$C_4$ alkyl; and hydrates and alcohol solvates thereof. The compounds of formula I as well as their disodium salts and alcohol solvates and hydrates thereof are described in WO 00/059863, along with methods for preparing them.

The disodium salt may be prepared from the ethanol solvate by evaporating or drying the ethanol solvate by methods known in the art to form the anhydrous disodium salt. Drying is generally carried out at a temperature of from about 80 to about 120° C., preferably from about 85 to about 90° C., and most preferably at about 85° C. The drying step is generally performed at a pressure of 26" Hg or greater. The anhydrous disodium salt generally contains less than about 5% by weight of ethanol and preferably less than about 2% by weight of ethanol, based on 100% total weight of anhydrous disodium salt. The disodium salt of the delivery agent can also be prepared by making a slurry of the delivery agent in water and adding two molar equivalents of aqueous sodium hydroxide, sodium alkoxide or the like. Suitable sodium alkoxides include, but are not limited to, sodium methoxide, sodium ethoxide, and combinations thereof. A still further method of preparing the disodium salt is by reacting the delivery agent with one molar equivalent of sodium hydroxide to yield the disodium salt. The disodium salt can be isolated as a solid by concentrating the solution containing the disodium salt to a thick paste by vacuum distillation. This paste may be dried in a vacuum oven to obtain the disodium salt of the delivery agent as a solid. The solid can also be isolated by spray drying an aqueous solution of the disodium salt. The delivery agents may be prepared by methods known in the art, e.g., as mentioned above, by methods described in U.S. Pat. Nos. 5,773, 647 and 5,866,536. The ethanol solvates, as described in the aforementioned WO 00/059863, include, but are not limited to, a molecular or ionic complex of molecules or ions of ethanol solvent with molecules or ions of the disodium salt of the delivery agent. Typically, the ethanol solvate contains about one ethanol molecule or ion for every molecule of disodium salt of the delivery agent. The ethanol solvate of the disodium salt of the delivery agent can be prepared by dissolving the delivery agent in ethanol. Typically, each gram of delivery agent is dissolved in from about 1 to about 50 mL of ethanol and generally, from about 2 to about 10 mL of ethanol. The delivery agent/ethanol solution is then reacted with a molar excess of a sodium containing salt, such as a monosodium containing salt, relative to delivery agent, i.e. for every mole of delivery agent there is more than one mole of sodium cations, yielding the ethanol solvate. Suitable monosodium salts include, but are not limited to, sodium hydroxide; sodium alkoxides, such as sodium methoxide and sodium ethoxide; and any combination of the foregoing. Preferably, at least about two molar equivalents of the monosodium containing salt are added to the ethanol solution, i.e. for every mole of delivery agent there is at least about two moles of sodium cations. Generally, the reaction is performed at or below the reflux temperature of the mixture, such as at ambient temperature. The ethanol solvate is then recovered by methods known is the art, such as, concentration of the resulting slurry at atmospheric distillation, cooling the concentrated slurry and filtering the solid. The recovered solid can then be vacuum dried to obtain the ethanol solvate. The hydrates of the disodium salts of the delivery agents may be prepared by drying the ethanol solvate to from an anhydrous disodium salt, as described above, and hydrating the anhydrous disodium salt. Preferably, the monohydrate of the disodium salt is formed. Since the anhydrous disodium salt is very hydroscopic, the hydrate forms upon exposure to atmospheric moisture. Generally, the hydrating step is performed at from about ambient temperature to about 50° C., preferably ambient temperature to about 30° C. and in an environment having at least 50% relative humidity. Alternatively, the anhydrous disodium salt may be hydrated with steam. The preferred delivery agents are N-(5-chlorosalicyloyl)-8-aminocaprylic acid (5-CNAC), N-(10-[2-hydroxybenzoyl]amino)decanoic acid (SNAD), N-(8-[2-hydroxybenzoyl]amino)caprylic acid (SNAC) and their monosodium and disodium salts, ethanol solvates of their sodium salts and the monohydrates of their sodium salts and any combinations thereof. The most preferred delivery agent is the disodium salt of 5-CNAC and the monohydrate thereof. Preferably the disodium salt is present in amount of more than 90% weight per total weight of the 5-CNAC present in the composition. The delivery agent, 5 CNAC, SNAD, and SNAC are very water soluble and nearly fully, i.e. greater than 90%, absorbed by the gastro-intestinal tract whether it is ingested in micronized or coarse form. However, it has been found, surprisingly, that when a micronized form of one of these carrier agents is employed in the composition, the absorption of the pharmacologically active agent of the present composition is more completely absorbed into the blood stream. Therefore, the use of micronized carrier agent is a required element of the present invention. A micronized form of the carrier agent, which is utilized in preparation of the solid oral dosage form of the present invention, is defined as a carrier agent which, when added to the present composition mixture of pharmacologically active agent and pharmaceutically inactive ingredients, has an average particle size of less than 40 micrometers. Desirably the carrier agent of the present invention has a micronized form which is defined as an average particle size of less than 20 microns. More interestingly, the carrier agent for the present invention has a micronized form which is defined as an average particle size of less than 10 microns. Micronized forms of the carrier agent of the present invention may be prepared by grinding it in a grinding mill which is acceptable for grinding pharmaceutical ingredients and which is capable of grinding the pharmaceutical ingredients and/or carrier agent to a fine and uniform micronized particle size. An example of such a grinding mill is an Air Jet Mill Gem T® (Copley Scientific, Ltd., Nottingham, UK). The finely ground carrier agent either separately or finely ground carrier agent plus any combination of finely ground additional ingredients of the present invention may then be screened, for example, over a mesh screen having the appropriate openings, in order to allow only those ingredients which have the required particle size to pass through and be collected for use in the present invention. The pharmaceutical compositions of the present invention typically contain a delivery effective amount of one or more of the delivery agents, i.e. an amount sufficient to deliver the active agent for the desired effect. Generally, the delivery agent is present in an amount of 2.5% to 99.4% by weight, more preferably 25% to 50% by weight.

Preferably a calcitonin, e.g. salmon calcitonin in free form or in salt form, is delivered as a pharmaceutical composition comprising calcitonin and a delivery agent for calcitonin. More preferably said pharmaceutical composition comprises a delivery agent selected from the group of 5-CNAC, SNAD, and SNAC. More preferably said pharmaceutical composition comprises a delivery agent is selected from the group consisting of a disodium salt of 5-CNAC, a disodium salt of SNAD, and a disodium salt of SNAC. More preferably, said pharmaceutical composition comprises a delivery agent in micronized form.

Alternatively, calcitonin can be orally delivered also with other technologies such as the one described in WO 94/26778; U.S. Pat. No. 5,359,030; U.S. Pat. No. 5,438,040; U.S. Pat. No. 5,681,811; U.S. Pat. No. 6,191,105; U.S. Pat. No. 6,309,633; U.S. Pat. No. 6,380,405; U.S. Pat. No. 6,436, 990; U.S. Pat. No. 6,458,776; and U.S. Pat. No. 6,479,692 (the content thereof is hereby incorporated by reference in its entirety). In short, such oral formulations relate generally to conjugation-stabilized (poly)peptide and protein compositions. More particularly, such oral delivery forms relate in one broad compositional aspect to covalently conjugated calcitonin complexes wherein the calcitonin is covalently bonded to one or more molecules of a polymer incorporating as an integral part thereof a hydrophilic moiety, e.g., a linear polyalkylene glycol, and wherein said polymer incorporates a lipophilic moiety as an integral part thereof. In one particular aspect, such oral delivery forms relate to a physiologically active calcitonin composition comprising a physiologically active peptide covalently coupled with a polymer comprising (i) a linear polyalkylene glycol moiety and (ii) a lipophilic moiety, wherein the peptide, linear polyalkylene glycol moiety, and the lipophilic moiety are conformationally arranged in relation to one another such that the physiologically active peptide in the physiologically active calcitonin composition has an enhanced in vivo resistance to enzymatic degradation, relative to the physiologically active calcitonin alone (i.e., in an unconjugated form devoid of the polymer coupled thereto). In another aspect, such oral delivery forms relate to a physiologically active calcitonin composition of three-dimensional conformation comprising a physiologically active calcitonin covalently coupled with a polysorbate complex comprising (i) a linear polyalkylene glycol moiety and (ii) a lipophilic moiety, wherein the physiologically active calcitonin, the linear polyalkylene glycol moiety and the lipophilic moiety are conformationally arranged in relation to one another such that (a) the lipophilic moiety is exteriorly available in the three-dimensional conformation, and (b) the physiologically active calcitonin in the physiologically active calcitonin composition has an enhanced in vivo resistance to enzymatic degradation, relative to the physiologically active calcitonin alone. In a further aspect, such oral delivery forms relate to a multiligand conjugated calcitonin complex comprising a triglyceride backbone moiety, having: a bioactive calcitonin covalently coupled with the triglyceride backbone moiety through a polyalkylene glycol spacer group bonded at a carbon atom of the triglyceride backbone moiety; and at least one fatty acid moiety covalently attached either directly to a carbon atom of the triglyceride backbone moiety or covalently joined through a polyalkylene glycol spacer moiety. In such multi ligand conjugated calcitonin complex, the d and B carbon atoms of the triglyceride bioactive moiety may have fatty acid moieties attached by covalently bonding either directly thereto, or indirectly covalently bonded thereto through polyalkylene glycol spacer moieties. Alternatively, a fatty acid moiety may be covalently attached either directly or through a polyalkylene glycol spacer moiety to the a and d carbons of the triglyceride backbone moiety, with the bioactive calcitonin being covalently coupled with the 13-carbon of the triglyceride backbone moiety, either being directly covalently bonded thereto or indirectly bonded thereto through a polyalkylene spacer moiety. In such a multiligand conjugated calcitonin complex, the bioactive calcitonin may advantageously be covalently coupled with the triglyceride modified backbone moiety through alkyl spacer groups, or alternatively other acceptable spacer groups, within the broad scope of the invention. As used in such context, acceptability of the spacer group refers to steric, compositional, and end use application specific acceptability characteristics. In yet another aspect such oral delivery forms relate to a polysorbate complex comprising a polysorbate moiety including a triglyceride backbone and functionalizing groups including: (i) a fatty acid group; and (ii) a polyethylene glycol group having a physiologically active moiety covalently bonded thereto, e.g., a physiologically active moiety is covalently bonded to an appropriate functionality of the polyethylene glycol group.

Such covalent bonding may be either direct, e.g., to a hydroxy terminal functionality of the polyethylene glycol group, or alternatively, the covalent bonding may be indirect, e.g., by reactively capping the hydroxy terminus of the polyethylene glycol group with a terminal carboxy functionality spacer group, so that the resulting capped polyethylene glycol group has a terminal carboxy functionality to which the physiologically active moiety may be covalently bonded. Such oral delivery forms relate to a further aspect to a stable, aqueously soluble, conjugated calcitonin complex comprising a physiologically active calcitonin covalently coupled to a physiologically compatible polyethylene glycol modified glycolipid moiety. In such complex, the physiologically active calcitonin may be covalently coupled to the physiologically compatible polyethylene glycol modified glycolipid moiety by a labile covalent bond at a tee amino acid group of the polypeptide. The physiologically compatible polyethylene glycol modified glycolipid moiety may advantageously comprise a polysorbate polymer, e.g., a polysorbate polymer comprising fatty acid ester groups selected from the group consisting of monopalmitate, dipalmitate, monolaurate, dilaurate, trilaurate, monoleate, dioleate, trioleate, monostearate, distearate, and tristearate. In such complex, the physiologically compatible polyethylene glycol modified glycolipid moiety may suitably comprise a polymer selected from the group consisting of polyethylene glycol ethers of fatty acids, and polyethylene glycol esters of fatty acids, wherein the fatty acids for example comprise a fatty acid selected from the group consisting of lauric, palmitic, oleic, and stearic acids. In the above complex, the physiologically active calcitonin may by way of illustration comprise a calcitonin selected from the group consisting of insulin, calcitonin, ACTH, glucagon, somatostatin, somatotropin, somatomedin, parathyroid hormone, erythropoietin, hypothalmic releasing factors, prolactin, thyroid stimulating hormones, endorphins, enkephalins, vasopressin, non-naturally occurring opiods, superoxide dismutase, interferon, asparaginase, arginase, arginine deaminease, adenosine deaminase ribonuclease, trypsin, chemotrypsin, and papain. In another aspect, the present invention relates to an oral administration dosage form for the mediation of insulin deficiency, comprising a pharmaceutically acceptable carrier and a stable, aqueously soluble, conjugated insulin complex comprising insulin or proinsulin covalently coupled to a physiologically compatible polyethylene glycol modified glycolipid moiety.

Furthermore, a further second alternative oral delivery dosage form which may be used according to the invention is a technology described in W0 97/33531; U.S. Pat. No. 5,912,014 and U.S. Pat. No. 608,618 (the content thereof is hereby incorporated by reference in its entirety). In short, such further oral delivery form protects calcitonin from the acidic environment and digestive enzymes as it passes through the stomach and intestine, and facilitates its entry into the bloodstream. Once it is safely in the bloodstream, calcitonin can exert its therapeutic effect. Such oral delivery form is e.g. a pharmaceutical composition for oral delivery of salmon calcitonin comprising: (A) a therapeutically effective amount of said salmon calcitonin; (B) at least one pharmaceutically acceptable pH-lowering agent; (C) at least one absorption enhancer effective to promote bioavailability of said salmon calcitonin; and (D) an enteric coating; wherein said pH-lowering agent is present in said pharmaceutical composition in a quantity which, if added to 10 milliliters of 0.1M aqueous sodium bicarbonate solutions would be sufficient to lower the pH of said solution to no higher than 5.5. The pharmaceutical composition, wherein said enteric coating is present at a weight which is no more than 20% of the weight of the remainder of said pharmaceutical composition excluding said enteric coating. The pharmaceutical composition of above, wherein said enteric coating is present at a weight which is no more than 5-15% of the weight of the remainder of said pharmaceutical composition excluding said enteric coating.

The pharmaceutical compositions with which the usefulness of calcitonin in the treatment of osteoarthritis is shown, may be provided as a capsule including a soft-gel capsule, tablet, caplet, suppository or other solid oral dosage form, all of which can be prepared by methods well known in the art.

The solid pharmaceutical compositions of the instant invention can be prepared by first grinding either the carrier agent or the carrier agent with any combination of the additional ingredients of the present composition to a micronized particle size. The micronized carrier agent or micronized carrier agent plus micronized additional ingredients of the present invention may then be further processed by conventional methods e.g. by blending a mixture of the active agent or active agents, the delivery agent, the crospovidone or povidone and other ingredients, kneading, and filling into capsules or, instead of filling into capsules, molding followed by further tableting or compression-molding to give tablets. In addition, a solid dispersion may be formed by known methods followed by further processing to form a tablet or capsule.

The following examples serve to further illustrate the invention and will be readily understood by one of ordinary skill in the art. The examples are not meant to be limiting of the present invention in any way.

EXAMPLES

A. Formulation Examples

Example 1

Formulation 1 (3 Batches)

Preparation of Micronized 5-CNAC: Coarse 5-CNAC, which is to be micronized, is added to a jet mill (Air Jet Mill Gem T® Copley Scientific, Ltd., Nottingham, UK) using a 80 ceramic pan cake jet mill, 8 cm diameter, 6 bar N2, 0.5 mm nozzles with manual feed of about 700 g/h. The coarse 5-CNAC is jet milled and periodically sampled under microscope with reference ruler measurements to identify when the average desired micronized particle size is obtained. Three different batches are ground to create 6 um, 35 um, and 46 um batches. Individual sieving of the separate micronized batches is then done by using a conical sieve mill (Quadro Comil, Quadro Engineering Incorporated 613 Colby Drive, Waterloo, Ontario, Canada N2V 1A1) with a U10, 813 um conical sieve, round beater, operating at 1500 upm with throughput of about 150 kg/h.

Formulation I-3. Salmon Calcitonin Formulation with 5-CNAC of Different Particle Size

| Ingredient | Amount (mg) | Percent (%) |
|---|---|---|
| Salmon Calcitonin | 1 | 0.25 |
| Micronized 5-CNAC | 228 | 57 |
| Avicel PH 102 ® | 147 | 36.75 |
| Crospovidone, NF | 20 | 5 |
| Magnesium stearate | 4 | 1 |
| Total | 400 | 100 |

Preparation of Formulation 1: Three different batches of tablets are prepared using the three different batches of micronized 5-CNAC disodium, one tablet batch having an average 5-CNAC disodium particle size of 46 microns (Batch A), a second tablet batch having an average 5-CNAC disodium particle size of 6 microns (Batch B), and a third tablet batch having an average 5-CNAC disodium particle size of 35 microns (Batch C).

0.50 g of salmon calcitonin, pre-screened through a 40 mesh screen, 57. g of micronized 5-CNAC disodium salt, screened through a 35 mesh screen, and 10 g of Polyplasdone XL (crospovidone, NF, International Specialty Products, 1361 Alps Road, Wayne, N.J., 07470, USA) is combined in a 500 mL jar and is mixed using a Turbula mixer for 100 revolutions at a speed of 46 RPM. An additional 57. g of micronized 5-CNAC disodium salt, screened through a 35 mesh screen, and 36.75 g of Avicel PH 102® is added to the jar and mixed for 500 revolutions at a speed of 46 RPM. A further 36.75 g of Avicel PH 102® is added to the jar and is mixed for an additional 100 revolutions at a speed of 46 RPM. 4.0 g of magnesium stearate is screened into the jar using a 35 mesh screen and is blended for 1 minute at a speed of 46 RPM. The final blend is compressed into tablets using a Manesty B3B tablet press. The tablet weight is approximately 400 mg.

The bioavailability of the tablets created in Example 1 may be tested as follows:

Example 2

Primate Administration

The tablets are prepared as in Example 1 using three different batches of micronized 5-CNAC disodium, one tablet batch having an average 5-CNAC disodium particle size of 46 microns (Batch A), a second tablet batch having an average 5-CNAC disodium particle size of 6 microns (Batch B), and a third tablet batch having an average 5-CNAC disodium particle size of 35 microns (Batch C). The tablets prepared from each of the three different batches are administered to the same four Rhesus monkeys separately on different days as follows:

The Rhesus monkeys fast overnight prior to dosing and are restrained in chairs fully conscious, for the duration of the study period. One tablet from Batch A or Batch B or Batch C is administered to each monkey via a gavage tube followed by 10 mL of water.

Rhesus monkey blood samples are collected immediately before administration and at 0.25, 0.5, 0.75, 1, 1.5, 2, 3, 4, 5, and 6 hours after administration. A tablet from each of the remaining two tablet batches is dosed and blood samples are collected in a similar manner but on a separate day for each of the remaining tablet batches. Resulting plasma salmon calcitonin for each dose and for each monkey is determined by radioimmunoassay. For each monkey, the primate plasma salmon calcitonin (SCt) for one batch and one time period, mean plasma SCt concentrations for all monkeys for one batch and one time period, Standard Deviation (SD) of plasma SCt concentrations for one batch and one time period, and Standard Error of the Mean (SEM) for plasma SCt concentrations for all monkeys for one batch and one time period are calculated and reported in Tables 1, 2, and 3 as follows.

TABLE 1

BATCH A: AVERAGE 5-CNAC PARTICLE SIZE 46 MICROMETERS
Salmon Calcitonin (SCt) Plasma Concentrations [pg/mL]
(Single Oral Tablet (200 mg 5-CNAC + 1 mg SCt) to the Rhesus Monkey)

| Animal no. | 0 | 0.25 | 0.50 | 0.75 | 1 | 1.5 | 2 | 3 | 4 | 5 | 6 |
|---|---|---|---|---|---|---|---|---|---|---|---|
| 1 | 0.0 | 17.8 | 91.7 | 279.7 | 449.2 | 278.8 | 48.0 | 10.5 | 5.3 | 3.3 | 0.0 |
| 2 | 0.0 | 117.4 | 535.0 | 430.8 | 981.4 | 1718.0 | 2396.4 | 719.5 | 253.6 | 102.1 | 62.9 |
| 3 | 0.0 | 113.9 | 754.5 | 1502.0 | 2351.0 | 2066.0 | 2684.4 | 1310.0 | 649.6 | 280.6 | 156.5 |
| 4 | 0.0 | 46.0 | 127.0 | 425.5 | 765.8 | 1102.0 | 1599.0 | 1022.0 | 419.3 | 87.0 | 23.4 |
| Mean | 0.0 | 73.8 | 377.1 | 659.5 | 1136.9 | 1291.2 | 1682.0 | 765.5 | 332.0 | 118.3 | 60.7 |
| SD | 0.0 | 49.7 | 322.2 | 566.0 | 838.4 | 783.8 | 1182.1 | 558.1 | 271.6 | 116.6 | 68.9 |
| SEM | 0.0 | 24.9 | 161.1 | 283.0 | 419.2 | 391.9 | 591.0 | 279.0 | 135.8 | 58.3 | 34.5 |

Lower Limit of Quantification (LLOQ) = 2.5 pg/mL, concentrations below LLOQ were set to zero for Table 1

TABLE 2

BATCH B: AVERAGE 5-CNAC PARTICLE SIZE 6 MICROMETERS
Salmon Calcitonin (SCt) Plasma Concentrations [pg/mL]
(Single Oral Tablet (200 mg 5-CNAC + 1 mg SCt) to the Rhesus Monkey)

| Animal no. | 0 | 0.25 | 0.50 | 0.75 | 1 | 1.5 | 2 | 3 | 4 | 5 | 6 |
|---|---|---|---|---|---|---|---|---|---|---|---|
| 1 | 0.0 | 265.6 | 315.8 | 245.6 | 357.2 | 1927.0 | 3010.0 | 863.2 | 139.4 | 48.5 | 20.8 |
| 2 | 0.0 | 607.0 | 777.0 | 1336.0 | 1602.0 | 4146.0 | 7521.0 | 2681.0 | 420.8 | 73.9 | 43.2 |
| 3 | 0.0 | 80.9 | 225.5 | 325.6 | 655.6 | 1478.0 | 3979.0 | 2775.0 | 520.2 | 91.5 | 41.3 |
| 4 | 0.0 | 286.4 | 155.3 | 237.7 | 241.0 | 269.7 | 294.2 | 321.0 | 179.8 | 67.5 | 13.6 |
| Mean | 0.0 | 310.0 | 368.4 | 536.2 | 714.0 | 1955.2 | 3701.1 | 1660.1 | 315.1 | 70.4 | 29.7 |
| SD | 0.0 | 218.5 | 280.2 | 534.7 | 617.2 | 1619.6 | 2986.3 | 1253.5 | 184.8 | 17.8 | 14.8 |
| SEM | 0.0 | 109.2 | 140.1 | 267.3 | 308.6 | 809.8 | 1493.1 | 626.7 | 92.4 | 8.9 | 7.4 |

Lower Limit of Quantification (LLOQ) = 2.5 pg/mL, concentrations below LLOQ were set to zero for Table 2

TABLE 3

BATCH C: AVERAGE 5-CNAC PARTICLE SIZE 35 MICROMETERS
Salmon Calcitonin (SCt) Plasma Concentrations [pg/mL]
(Single Oral Tablet (200 mg 5-CNAC + 1 mg SCt) to the Rhesus Monkey)

| Animal no. | Time [hours] | | | | | | | | | | |
|---|---|---|---|---|---|---|---|---|---|---|---|
| | 0 | 0.25 | 0.50 | 0.75 | 1 | 1.5 | 2 | 3 | 4 | 5 | 6 |
| 1 | 0.0 | 36.1 | 94.7 | 428.0 | 739.4 | 2568.0 | 4025.0 | 1348.0 | 499.6 | 218.4 | 98.1 |
| 2 | 0.0 | 10.9 | 55.0 | 168.9 | 248.2 | 507.3 | 654.0 | 434.8 | 177.3 | 68.8 | 38.9 |
| 3 | 0.0 | 172.3 | 336.6 | 409.5 | 584.9 | 1487.0 | 2087.0 | 1479.0 | 162.0 | 52.0 | 17.2 |
| 4 | 0.0 | 7.9 | 46.9 | 208.1 | 390.1 | 1237.0 | 2347.0 | 1342.0 | 192.3 | 42.3 | 19.2 |
| Mean | 0.0 | 56.8 | 133.3 | 303.6 | 490.7 | 1449.8 | 2278.3 | 1151.0 | 257.8 | 95.4 | 43.4 |
| SD | 0.0 | 78.0 | 137.1 | 134.1 | 215.8 | 853.5 | 1382.1 | 481.6 | 161.7 | 82.7 | 37.8 |
| SEM | 0.0 | 39.0 | 68.6 | 67.1 | 107.9 | 426.7 | 691.1 | 240.8 | 80.8 | 41.4 | 18.9 |

Lower Limit of Quantification (LLOQ) = 2.5 pg/mL, concentrations below LLOQ were set to zero for Table 3

Example 3

Preparation of Formulations 2-4

Alternatively, there are further formulations provided:

Formulation 2:

| Ingredient | Amount (mg) |
|---|---|
| sCT | 0.25 |
| 5-CNAC (micronized) | 28.5 |
| Avicel PH102 | 238.25 |
| Crospovidone XL | 15 |
| Pluronic F68 | 3 |
| Cab-O-Sil | 3 |
| Talc | 6 |
| Mg Stearate | 6 |
| Total | 300 |

Formulation 3:

| Ingredient | Amount (mg) |
|---|---|
| sCT | 0.5 |
| 5-CNAC (micronized) | 28.5 |
| Avicel PH102 | 238 |
| Crospovidone XL | 15 |
| Pluronic F68 | 3 |
| Cab-O-Sil | 3 |
| Talc | 6 |
| Mg Stearate | 6 |
| Total | 300 |

Formulation 4:

| Ingredient | Amount (mg) |
|---|---|
| sCT | 0.5 |
| 5-CNAC (non-micronized) | 28.5 |
| Avicel PH102 | 238 |
| Crospovidone XL | 15 |
| Pluronic F68 | 3 |
| Cab-O-Sil | 3 |
| Talc | 6 |
| Mg Stearate | 6 |
| Total | 300 |

The process for preparation of the above formulations are similar to that of the one, described in Example 1. However, since there are a few more components for the current formula, there is some deviation which are described below:

1 Pre Weigh 0.3 g of sCT, pass sCT through #60 mesh screen
2 Weigh 0.25 g of screened sCT DS
3 Blend sCT and Crospovidone in a suitable container using Turbula Mixer, blend for 10 mins
4 Pass through #45 mesh screen
5 Add 5-CNAC to Blend from step #3, blend for 10 mins
6 Pass through #35 mesh screen
7 Add half Avicel into Blend #5, blend for 10 mins
8 Pass through #35 mesh screen
9 Add remaining of Avicel, Pluronic F68, and Cab-O-Sil blend for 20 mins
10 Add Talc and Mg Stearate into the above blend and blend for 2 mins All the equipments used are the same as described in Example 1.

Example 4

Preparation of Formulation 5

Alternative formulation is presented shortly presented below: 0.502 of salmon calcitonin, pre-screened through a 40 mesh screen, 120 g of 5-CNAC disodium salt, pre-screened through a 35 mesh screen, and 20 g of Polyplasdone XL (crospovidone, NF) is combined in a 500 mL jar and is mixed using a Turbula mixer for 2 minutes at a speed of 46 RPM. An additional 125.4 g of 5-CNAC disodium salt, pre-screened through a 35 mesh screen, and 32.5 g of Avicel PH 102 is added to the jar and is mixed for a period of 8 minutes at a speed of 46 RPM. A further 32.5 g of Avicel is added to the jar and is mixed for 5 minutes at a speed of 46 RPM. 4.0 g of magnesium stearate is screened into the jar using a 35 mesh screen and is blended for 1 minute at a speed of 46 RPM. The final blend is compressed into tablets using a Manesty B3B tablet press. The tablet weight is approximately 400 mg.

Example 5

Preparation of Formulation 6

An alternative formulation comprising salmon calcitonin suitable for nasal administration:

| Ingredient | Quantity (per ml) |
|---|---|
| 1) Salmon calcitonin (active ingredient) 10% excess | 0.1375 mg |
| 2) NaCl | 0.01375 mg |
| 3) Benzalkonium chloride | 0.15125 mg |
| 4) HCl (1 N) added to pH 3.7 | 7.5 mg |
| 5) Distilled water to an end volume of 1.0 ml. | 0.1 mg |

Components 1 to 3 are combined under protection of nitrogen gas (on a scale to produce a final volume of 2500 ml) in conventional manner, with 10% of salmon calcitonin being added to allow for loss at filtration. 4) is then added to bring the pH to 3.7 and distilled water added to an end-volume of 2500 ml. The obtained solution is filtered (e.g. using a 0.2 .mu.m filter) to give a composition suitable for nasal application and for filling into a spray nasal dispenser with a solution volume of 2 ml.

Example 6

Preparation of Formulation 7

Suppositories containing 300 I.U. (International Units) of salmon calcitonin are prepared according to e.g. U.S. Pat. No. 5,149,537 (the content of which is incorporated by its entirety) containing the following composition per suppository:

| Ingredient | Mg/Suppository |
|---|---|
| Salmon calcitonin (300 I.U.) | 0.0692.sup.+ (1 mg substance contains 4767 I.U. (overage of 10% used) |
| Anhydrous citric acid | 0.78 |
| Trisodium citrate dihydrate | 0.50 |
| Mannitol | 48.651 |
| Sodium taurocholate | 30.0 |
| Suppository base A | 1420.0 |
| | 1500 mg |

As suppository base A may be used cocoa butter. It is preferred to use synthetic or semi-synthetic suppository bases. These may be water insoluble fats, e.g. glycerides (mono-, di- and/or tri-) of fatty acids, e.g. made from coconut oil or palm kern oil.

Straight Chain $C_{10-18}$ fatty acid glycerides, conveniently saturated are preferred. Examples are Witepsol (Registered Trade Mark), e.g. Witepsol H series available from Dynamit Nobel, W. Germany; Suppocire (Registered Trade Mark), e.g. Suppocire AM or AS2, available from Gattefosse, France and Novata (Registered Trade Mark), e.g. Novata BD, available from Henkel GmbH, W. Germany.

Alternatively, the Guerbet alcohols and water soluble suppository bases such as polyethyleneglycol may be used.

Preferably the suppository base has a low melting range, e.g. 30 to 36° C.

Preparation Procedure a) Preparation of Granulate (for 3,500 doses)

0.2423 g of the calcitonin, 2.73 g of the citric acid, 1.75 g of the tri-sodium salt are mixed in the dry state and dissolved in 14.0 g water. 170.3 g of sieved mannitol is added (AS 700 microns, WD 120 microns). The mass is kneaded and sieved (AS 1,600 microns, WD 450 microns). The des-agglomerated powder is dried at 40. ° C. for 25 minutes, and sieved (AS 450 microns, AS 120 microns) to give 167 g of a powder.

b) Addition of Enhancer and Molding (for 3,000 Doses)

150 g of the powder obtained from step a) and 90 g of ground sodium taurocholate as mixed, sieved (AS 250; WD 100 microns), and mixed again. The mixture is added to 4260 g of melted suppository base A at 38° C. Homogenization is effected (Polyton apparatus, speed setting 4) for 3 minutes. The mass is transferred at 33° C. to a pre-warmed vessel in a suppository making machine (BONAPACE).

The suppositories are molded at from 33 to 33.5° C. in neutral polyvinylchloride foil (or aluminium foil) in doses of about 1.5 ml and weight 1.5 g. Cooling is effected with an air stream at 20° C. Yield 2,590 suppositories. Disintegration time 6 minutes. Melting point 34.9° C. Hardness 81N at 20° C., pH in water 4.2.

B. Example Showing Efficacy of Calcitonin in Osteoarthritis

Example 7

Clinical Trial 36 osteoarthritic patients completing the trial are included in a 12 weeks (84 days) double blind, placebo controlled, monocenter, parallel study. The objective is to assess in vivo the effects of an oral formulation of calcitonin on biochemical markers of bone, cartilage and synovium metabolism in human osteoarthritis. Patients are divided in three groups: two groups treated with oral calcitonin either 0.5 mg or 1 mg once daily and one control group receiving a placebo.

The Inclusion Criteria are (Table 4):
Females either over 55 years of age or over 50 years of age and at least 5 years menopausal (natural or surgical).
Males over 50 years of age. Those having intercourse with a woman who is not postmenopausal will have to use barrier contraception during the whole time period of the study and continuing for 4 weeks after the completion of the study.
Patients suffering from active osteoarthritis of the hip and/ or knee. Hyperactivity of the diseased joint documented in recent (=6 months before study start) bone scintigrams is mandatory.
Patients with at least moderate pain on active movement (greater than or equal at 10 on the LEQUESNE scale (see M G Lequesne, 1997, J of Rheumatology 24: 779-781)
Patients having read the information sheet and signed the consent form.

The Exclusion Criteria are (Table 5):
Patients suffering from acute osteoarthritis and requiring intervention of arthroplasty during the course of the study or requiring joint immobilization for several weeks prior to or during the study period.
Patients suffering from crystal deposit diseases or with known hereditary or congenital defects.
Patients suffering from clinical significant hepatic, renal, cardiovascular, psychiatric, endocrine and/or hematological diseases.
Patients suffering from any other systemic or local disease judged to be incompatible with the present protocol by the investigator.
Patients with abnormal laboratory values judged as clinically significant Patients who have received any intra-articular injection or systemic administration of corticosteroids during the 8 weeks before the study start.

Patients with a known history of alcohol and/or drug abuse or those unlikely to cooperate with the investigator in accordance with the study protocol.

The Study End-Points are (Table 6):

The primary study end-points are the circulating levels of the human markers of cartilage, synovium and bone metabolism.

The secondary study end-points are the drug treatment efficacy and tolerability, as assessed by the patient and investigator.

Additionally safety assessments consist of monitoring and recording all adverse events and serious adverse events, the regular monitoring of hematology, blood chemistry and urine values, regular measurement of vital signs and the performance of physical examinations.

The study procedure: Following a 2 weeks pre-treatment wash-out period, during which only paracetamol is allowed to be taken at the maximum daily dosage of 3000 mg, each patient is randomized to the intake of either placebo or one of the two dosages of the oral formulation of calcitonin. During the 12 weeks treatment period, the patient is allowed to take paracetamol in case of need at a maximum daily dosage of 3000 mg.

The Patients' Evaluation Time-Points are (Table 7):

Visit 1: day-14: Screening visit. Start of wash-out period.
Visit 2: day 0: Baseline visit. Start of treatment.
Visit 3: day 14: 2 weeks of treatment completed.
Visit 4: day 42: 6 weeks of treatment completed.
Visit 5: day 84: Final visit. 12 weeks of treatment completed.

The Type of Evaluations (Table 8):

At visits 2, 3, 4 and 5, the second fasting urine of the morning as well as plasma, serum and synovial fluid (if any) are sampled and analyzed for cartilage, synovium and bone metabolism markers by specific immunoassays.

Adverse events are recorded at visits 3, 4 and 5.

One or more (knee or hip) joints are evaluated by the LEQUESNE questionnaire at visit 1 (screening visit), and documented as eligible for selection at the next visit, on the basis of pain intensity under active movement. At visit 2 (baseline visit) these eligible joints are reassessed and the most painful joint for which the pain intensity is equal or above 10 on the LEQUESNE questionnaire, is selected as the target joint.

The drug efficacy on the target joint are made on the basis of the evolution of the pain intensity between visits 2 and 5 (related to the pain intensity at visit 1) by a clinical examination and the LEQUESNE questionnaire.

Regarding treatment efficacy evaluation, the quantity of rescue medication (paracetamol) taken by the patient during the 12 weeks treatment period is considered.

Drug efficacy and tolerability is additionally assessed and patient at visits 3, 4 and 5 by means of 2 separate VAS scales (see Huskinson E. C., 1974, The Lancet: 1127-1131)

Example 8

3-Month Treatment with Oral Salmon Calcitonin Suppresses Urinary Collagen Type II Degradation Products in Postmenopausal Women Subjects and Methods: The study population consists of 152 generally healthy Danish postmenopausal women 55-85 years old, who have been postmenopausal for at least 5 years. Women receive treatment with either daily (0.15, 0.4, 1.0, or 2.5 mg) orally dosed sCT (see below for pharmaceutical compositions) combined with eligen technology-based carrier molecule (200 mg), or placebo for 3 months. All participants receive a calcium supplement of 1000 mg plus 400 IU of vitamin D daily throughout the study. Efficacy parameters are 24 hours urinary C-terminal telopeptide of collagen type I (CTX-1) and CTX-II corrected for creatinine excretion assessed at baseline and after 3-month therapy.

| Pharmaceutical Compositions comprising salmon calcitonin used in study | | | | |
|---|---|---|---|---|
| Ingredient | Amount per tablet (mg) | | | |
| Salmon Calcitonin | 0.15 | 0.4 | 1 | 2.5 |
| 5-CNAC-disodium salt (non-micronized) | 228 | 228 | 228 | 228 |
| Microcrystalline cellulose, NF (Avicel PH-102) | 147.85 | 147.6 | 147 | 145.5 |
| Crospovidone, NF | 20 | 20 | 20 | 20 |
| Magnesium Stearate, NF, EP | 4 | 4 | 4 | 4 |
| Total | 400 | 400 | 400 | 400 |

Manufacturing Process:
i) Weigh 5-CNAC and divide into 2 equal parts and label as A and B.
ii) Weigh Avicel and divide into 2 equal parts and label as A and B.
1) Place crospovidone on a 35 mesh screen. Place pre-weighed calcitonin on top of crospovidone, then add part A of 5-CNAC.
2) Screen crospovidone/calcitonin/5-CNAC and transfer into suitable size blender and blend for 500 revolutions.
3) Screen part B of 5-CNAC through 35 mesh screen.
4) Add part B of screened 5-CNAC and part A of Avicel to mixed blend from step 2) and blend for 800 revolutions.
5) Add part B of Avicel to above blend from step 4) and blend for 500 revolutions.
6) Screen magnesium stearate through 35 mesh screen and add to blended powders from step 5) and blend for 100 revolutions.

Results: There are no significant differences in the different intervention groups of sCT in terms of age, BMI, baseline urinary concentration of CTX-I and CTX-II. There is a clear and significant dose dependent relationship in 24 hours urinary CTX-II response to oral sCT (ANOVA=0.012). Compared to placebo, the 1.0 mg daily group reveales the greatest decrease in urinary CTX-II after 3-month treatment (−19.7%, p=0.009). The women who receive 0.4 mg and 2.5 mg of sCT also have significant decreases in urinary CTX-II (−15.2%, p=0.04, and −17.5%, p=0.02, respectively). Similar dose-dependent responses are found in 24-hour urinary CTX-I at 3-month treatment. Women receiving 1.0 mg of sCT also have the greatest reduction in 24-hours urinary CTX-I (41.0%, p<0.001) compared to women in placebo group. When stratifying the study population into tertiles of baseline urinary CTX-II, the mean of urinary CTX-II in the different tertiles was 114.6, 197.9 and 385.4 ng/mmol, respectively. Women in the highest tertile of urinary CTX-II at baseline show the largest responses to oral sCT in a dose-dependent manner. Women, who received 1.0 mg of sCT, and are in the highest cartilage turnover at baseline, have the greatest decreases in urinary CTX-II after 3-month treatment compared to women in the lowest tertile (−36.6% vs. −9.9%, p=0.005). Similar trend is observed with 0.4 mg sCT when comparing women in the highest tertile of urinary CTX-II to the lowest tertile.

C-telopeptide of type I collagen (CTX I) is considered to be a specific marker sensitive to bone resorption; conversely, type II collagen C-telopeptide (CTX-II) is considered to be a useful cartilage marker.

Conclusion: Our study strongly suggests that salmon CT may reduce cartilage degradation and thereby could provide therapeutic benefits for osteoarthritis in a dose range of 0.4 to 2.5 mg of salmon calcitonin, more preferably around 1 mg of salmon calcitonin.

The invention claimed is:

1. A method of treating osteoarthritis in a human in need thereof comprising orally administering to said human a pharmaceutical composition comprising salmon calcitonin in free or salt form and a delivery agent selected from the group consisting of N-(5-chlorosalicyloyl)-8-aminocaprylic acid (5-CNAC), N-(10-[2-hydroxybenzoyl]amino)decanoic acid (SNAD), N-(8-[2-hydroxybenzoyl]amino)caprylic acid (SNAG), and disodium salts thereof, wherein the amount of said salmon calcitonin in said pharmaceutical composition is between 0.4 and 1.2 mg.

2. The method according to claim 1, wherein the pharmaceutical composition further comprises at least one pharmaceutically acceptable pH-lowering agent, at least one absorption enhancer, and an enteric coating.

3. The method according to claim 1, wherein the delivery agent is a disodium salt of 5-CNAC, a disodium salt of SNAD or a disodium salt of SNAC.

4. The method according to claim 3, wherein the delivery agent is in micronized form.

5. The method according to claim 1, wherein the amount of said salmon calcitonin in said pharmaceutical composition is between 0.8 and 1.2 mg.

6. The method according to claim 5, wherein the delivery agent is selected from the group consisting of a disodium salt of 5-CNAC, a disodium salt of SNAD and a disodium salt of SNAC.

7. The method according to claim 6, wherein the delivery agent is a disodium salt of 5-CNAC.

8. The method according to claim 5, wherein the amount of said salmon calcitonin in said pharmaceutical composition is about 1 mg.

9. The method according to claim 8, wherein the delivery agent is selected from the group consisting of a disodium salt of 5-CNAC, a disodium salt of SNAD and a disodium salt of SNAC.

10. The method according to claim 9, wherein the delivery agent is a disodium salt of 5-CNAC.

11. A method of preserving and stimulating cartilage in a human having osteoarthritis comprising orally administering to said human a pharmaceutical composition comprising salmon calcitonin in free or salt form and a delivery agent selected from the group consisting of 5-CNAC, SNAD, SNAG, and disodium salts thereof, wherein the amount of said salmon calcitonin in said pharmaceutical composition is between 0.4 and 1.2 mg.

* * * * *